United States Patent [19]

Torii et al.

[11] Patent Number: 4,810,788

[45] Date of Patent: Mar. 7, 1989

[54] AZETIDINONE DISULFIDE DERIVATIVES AND A PROCESS FOR PREPARING THE SAME

[75] Inventors: Sigeru Torii; Hideo Tanaka; Junzo Nokami; Michio Sasaoka, all of Okayama; Norio Saito, Tokushima; Takashi Siroi, Okayama, all of Japan

[73] Assignee: Otsuka Kagaku Yakuhin Kabushiki Kaisha, Osaka, Japan

[21] Appl. No.: 46,423

[22] Filed: May 6, 1987

Related U.S. Application Data

[60] Division of Ser. No. 908,970, Sep. 17, 1986, abandoned, which is a continuation of Ser. No. 553,306, Nov. 17, 1983, abandoned.

[30] Foreign Application Priority Data

Nov. 29, 1982 [JP] Japan .................... 57-210490

[51] Int. Cl.[4] .................. C07D 205/08; C07D 401/12; C07D 401/14; C07D 403/12
[52] U.S. Cl. ..................... 540/358; 540/353
[58] Field of Search ........................ 540/358

[56] References Cited

U.S. PATENT DOCUMENTS 3,954,732 5/1976 Kamiya ................ 540/358

Primary Examiner—Mark L. Berch
Attorney, Agent, or Firm—Larson and Taylor

[57] ABSTRACT

An azetidinone derivative represented by the formula (I)

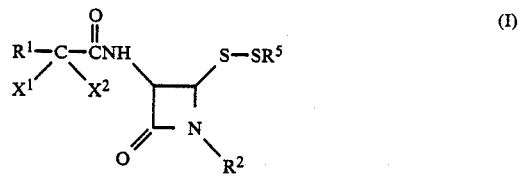

wherein $R^1$ is substituted or unsubstituted phenyl or substituted or unsubstituted phenoxy, $R^2$ is hydrogen, optionally substituted hydrocarbon residue or amino-protecting group selected from acyl, silyl, sulfonyl and phosphonyl derived from organic or inorganic acid,

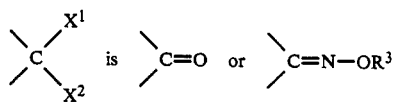

(wherein $R^3$ is hydrogen or lower alkyl), $X^1$ and $X^2$ are the same or different and are halogen, hydroxyl, alkoxy, acyloxy, $SR^4$ (wherein $R^4$ is straight chain or branched chain lower alkyl substituted or unsubstituted, substituted or unsubstituted phenyl or substituted or unsubstituted heterocyclic group), amino or hydrogen, one of $X^1$ and $X^2$ being hydrogen when the other is not, and $R^5$ is substituted or unsubstituted phenyl or substituted or unsubstituted heterocyclic group, and a process for preparing the same.

1 Claim, No Drawings

AZETIDINONE DISULFIDE DERIVATIVES AND A PROCESS FOR PREPARING THE SAME

This is a division of application Ser. No. 908,970 filed Sept. 17, 1986, now abandoned, which is a continuation of application Ser. No. 553,306, which was filed on Nov. 17, 1983, now abandoned.

This invention relates to azetidinone derivatives and a process for preparing the same and more particularly to novel azetidinone derivatives represented by the formula (I)

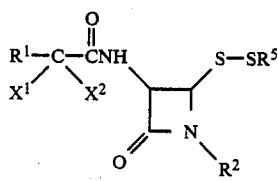 (I)

wherein $R^1$ is substituted or unsubstituted phenyl or substituted or unsubstituted phenoxy, $R^2$ is hydrogen, optionally substituted hydrocarbon residue or amino-protecting group selected from acyl, silyl, sulfonyl and phosphonyl derived from organic or inorganic acid,

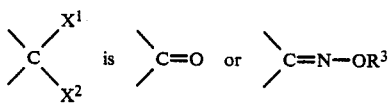

(wherein $R^3$ is hydrogen or lower alkyl), $X^1$ and $X^2$ are the same or different and are halogen, hydroxyl, alkoxy, acyloxy, $SR^4$ (wherein $R^4$ is straight chain or branched chain lower alkyl substituted or unsubstituted, substituted or unsubstituted phenyl or substituted or unsubstituted heterocyclic group), amino or hydrogen, one of $X^1$ and $X^2$ being hydrogen when the other is not, and $R^5$ is substituted or unsubstituted phenyl or substituted or unsubstituted heterocyclic group, and a process for preparing the same.

The azetidinone derivatives of the formula (I) of the present invention are novel compounds undisclosed in literature. While numerous processes have been heretofore developed for synthesizing azetidinone derivatives of the formula (I) wherein $X^1$ and $X^2$ are each hydrogen, a process is still unknown for synthesizing the derivatives of the formula (I) wherein at least one of $X^1$ and $X^2$ is a functional group. Generally there are various types of cephalosporin compounds having an antibacterial action and thus useful as an antibacterial agent which have a functional group such as amino, imino, hydroxy or like group on the amido chain at the 7-position. Conventionally the introduction of an imido chain having a functional group has been conducted by deacylating the amido group at the 7-position to convert it into an amine group and introducing

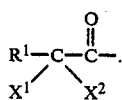

The azetidinone derivatives of the formula (I) of the present invention having the amido group with the required functional group can be converted directly into a cephalosporin compound having the required functional group, as seen from a reaction equation to be shown later.

An object of the present invention is to provide the novel azetidinone derivatives of the formula (I) having a functional group on the amido chain.

Another object of the invention is to provide a process for preparing the novel azetidinone derivatives of the formula (I).

Other features of the present invention will become apparent from the following description.

According to the present invention, the contemplated compounds of the formula (I) can be prepared by reacting a thiazolinoazetidinone derivative represented by the formula (IV)

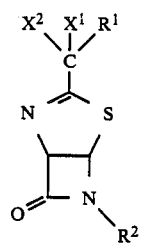 (IV)

wherein $R^1$, $R^2$, $X^1$ and $X^2$ are as defined above with a disulfide represented by the formula (V)

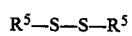 (V)

wherein $R^5$ is as defined above in a hydrous organic solvent in the presence of an acid.

Specific examples of the groups represented by $R^1$ in the compound of the formula (IV) serving as the starting material in the present invention are phenyl, tolyl, xylyl, p-chlorophenyl, p-nitrophenyl and like substituted or unsubstituted phenyl groups; phenoxy, tolyloxy, xylyloxy, p-chlorophenoxy, p-nitrophenoxy and like substituted or unsubstituted phenoxy groups, etc.

Examples of the groups represented by $R^2$ are hydrogen, optionally substituted hydrocarbon residue or amino-protecting group such as acyl, silyl, sulfonyl, phosphonyl and the like, derived from organic or inorganic acid. Examples of the optionally substituted hydrocarbon residues are those having the respective formulae

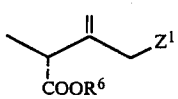 (II)

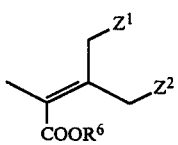 (III)

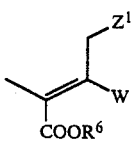 (VI)

wherein $R^6$ is hydrogen or carboxyl-protecting group, $Z^1$ and $Z^2$ are the same or different and are each hydrogen, halogen, groups containing sulfur, oxygen, nitrogen or the like, and W is protected hydroxyl group. Examples of the carboxyl-protecting groups represented by $R^6$ are benzyl, p-nitrobenzyl, p-methoxybenzyl, diphenylmethyl, triphenylmethyl and like phenylmethyl groups; phenoxymethyl, p-nitrophenoxymethyl, p-methoxyphenoxymethyl and like phenyloxymethyl groups; methyl, ethyl, tert-butyl, 2-chloroethyl, 2,2,2-trichloroethyl and like substituted or unsubstituted lower alkyl groups; etc. Examples of the substituents represented by $Z^1$ and $Z^2$ are bromine, chlorine, fluorine and like halogen atoms; methylthio, ethylthio, phenylthio, p-nitrophenylthio, pentachlorophenylthio, 2-pyridylthio, 2-benzothiadiazolylthio, 1,3,4-thiadiazole-5-ylthio, 2-substituted-1,3,4-thiadiazole-5-ylthio, 1,2,3,4-tetrazole-5-ylthio, 1-substituted-1,2,3,4-tetrazole-5-ylthio, O-ethyldithiocarbonate, N,N-diethyldithiocarbamate, phenylsulfonyl, p-methylphenylsulfonyl and like groups containing sulfur; hydroxy, methoxy, ethoxy, acetoxy, benzoyloxy, nitrosooxy, nitriloxy and like groups containing oxygen; dimethylamino, piperidine-1-yl and like groups containing nitrogen; etc. Examples of the protected hydroxyl groups represented by W are diphenylphosphonyloxy, methanesulfonate, N-morphonyl, diphenylmethyloxy and the like.

Examples of the groups represented by $R^3$ are methyl, ethyl, propyl, isobutyl, tert-butyl and like lower alkyl groups, etc.

Examples of the atoms or groups represented by $X^1$ are chlorine, bromine, fluorine and like halogen atoms; hydroxyl, methoxy, ethoxy, propoxy, butoxy, isobutoxy, tert-butoxy and like alkoxy groups; acetoxy, propionyloxy, butyloxy, isobutyloxy and like acyloxy groups; methylamino, dimethylamino, ethylamino, diethylamino, propylamino, dipropylamino, butylamino, dibutylamino, cyclohexylamino and like amino groups; methylthio, ethylthio, isopropylthio, tert-butylthio, phenylthio, p-nitrophenylthio, pentachlorophenylthio, 2-pyridylthio, 2-benzothiazolylthio, 2-substituted-1,3,4-thiadiazole-5-ylthio, 1-substituted-1,2,3,4-tetrazole-5-ylthio and like groups of $SR^4$, etc.

Examples of the atoms or groups represented by $X^2$ are the same as those described above in respect of $X^1$ or hydrogen.

The compounds of the formula (IV) which are known and serve as the starting material can be prepared from azetidinone derivatives of the formula (VII)

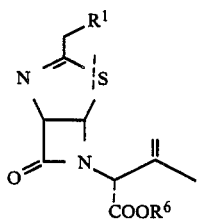

(VII)

wherein $R^1$ and $R^6$ are as defined above by the conventional method [e.g., the method as disclosed in Tetrahedron Letter, 3193 (1981)] or also can be prepared by further treating the compounds thus obtained in the usual manner.

Examples of the disulfides represented by the formula (V) which are used in the foregoing reaction are those wherein $R^5$ is substituted or unsubstituted phenyl or substituted or unsubstituted heterocyclic group. Examples of the substituted or unsubstituted phenyl groups are phenyl, p-nitrophenyl, pentachlorophenyl, trichlorophenyl, etc. Examples of the substituted or unsubstituted heterocyclic groups are 2-pyridyl, 2-benzothiazolyl, 1,3,4-thiadiazole-2-yl, 5-methyl-1,3,4-thiadiazole-2-yl, 5-phenyl-1,3,4-thiadiazole-2-yl, 1,2,3,4-tetrazole-5-yl, 1-methyl-1,2,3,4-tetrazole-5-yl, 1-phenyl-1,2,3,4-tetrazole-5-yl, benzimidazolyl, etc.

The amounts of the compounds of the formula (IV) and the compound of the formula (V) to be used are not particularly limited and can be suitably determined over a wide range. The latter is used in an amount of usually about 1 to about 10 moles, preferably about 1 to about 2 moles, per mole of the former.

The reaction of the present invention is conducted in a hydrous organic solvent in the presence of an acid. The water content in the hydrous organic solvent, although not particularly limitative, is about 1 to about 1000 equivalents, preferably about 10 to about 500 equivalents, based on the compound of the formula (IV). Examples of useful organic solvents are pentane, hexane, benzene, toluene and like hydrocarbons; methylene chloride, chloroform, carbon tetrachloride, dichlorobenzene and like halogenated hydrocarbon; methyl formate, methyl acetate, ethyl acetate, butyl acetate and like esters; diethyl ether, dimethyl ether, tetrahydrofuran, dioxane and like ethers; methanol, ethanol, butanol, ethylene glycol and like alcohols; formic acid, acetic acid, propionic acid and like carboxylic acids; acetonitrile, benzonitrile and like nitriles; dimethylformamide, dimethylacetamide and like amides; dimethyl sulfoxide and like sulfoxides; nitromethane, nitroethane and like nitrohydrocarbons; acetone, cyclohexanone and like ketones; etc. These organic solvents can be used singly or in mixture. Among these solvents, it is preferred to use ether, ketone, alcohol, amide, sulfoxide or like hydrophilic polar solvents or a mixture of at least one of such hydrophilic solvents with at least one of the above other solvents. The amount of the solvent is usually about 1 to about 1000 parts, preferably about 2 to about 500 parts, by weight, based on the weight of the compound of the formula (IV), although variable depending upon the kinds of the starting compound of the formula (IV) and the disulfide of the formula (V).

Useful acids include a wide variety of organic or inorganic acids having an acidity sufficient to decompose the thiazoline ring of the compound of the formula (I), such as hydrogen halide, sulfuric acid, nitric acid, phosphoric acid, perchloric acid, hydrochloric acid and like mineral acids, alkanesulfonic acid, arylsulfonic acid, arylalkylsulfonic acid, α-haloalkanesulfonic acid and like sulfonic acid; α-halocarboxylic acid, polycarboxylic acid and like carboxylic acids; etc. Preferable of these acids are those having a dissociation constant of over about 0.01. Among them, particularly preferable are perchloric acid, trifluoroacetic acid, trichloroacetic acid, dichloroacetic acid, trifluoromethanesulfonic acid, trichloromethanesulfonic acid, hydrochloric acid, hydrobromic acid, sulfuric acid, hydrofluoric acid, nitric acid, phosphoric acid, benzenesulfonic acid, toluenesulfonic acid, etc. The amount of the acid, although variable depending on the kind of the compound of the formula (IV and solvent, the reaction temperature and other conditions, is usually about 0.01 to about 50 moles, preferably about 0.1 to about 10 moles, per mole of the compound of the formula (IV).

When a side reaction is caused by the decomposition of the azetidinone ring or amino-protecting group represented by $R^2$, the desired compound can be prepared in high yields by suitably determining the reaction conditions such as the kind and concentration of the acid, reaction temperature, reaction time, etc.

The reaction between the compounds of the formulae (IV) and (V) is conducted generally at room temperature and is completed usually in about 10 minutes to about 3 hours. When the compound of the formula (I) wherein

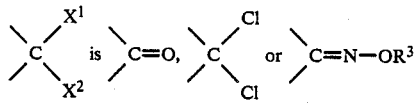

is prepared, the reaction is performed at room temperature for about 24 to about 120 hours or at about 30° to about 80° C. for about 1 to about 48 hours, whereby the compound of the formula (I) can be produced in a high yield.

The examples of the groups represented by $R^1$, $R^2$, $X^1$, $X^2$ and $R^5$ in the present compounds of the formula (I) are the same as those exemplified above in respect of the compounds of the formulae (IV) and (V).

The process of the present invention essentially involves the reaction between the compound of the formula (IV) and the compound of the formula (V). The compound of the formula (I) can not be prepared, as seen from Comparison Example to be described later, when reacting in the same manner as above the compound of the formula (IV) with a compound of the formula (VIII)

$$R^5-S-Cl \qquad (VIII)$$

wherein $R^5$ is as defined above in place of the compound of the formula (V).

After completing the reaction, the contemplated compound thus produced is extracted and separated from the reaction mixture in the usual manner and can be easily purified by precipitation, filtration, recrystallization, chromatography, etc.

The azetidinone derivatives of the formula (I) of the present invention are useful as intermediates for synthesizing cephalosporin-type antibiotics. For example, the azetidinone derivative of the formula (I) wherein $R^2$ is a group of

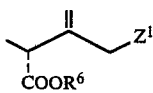

[to be hereinafter referred to as a compound of the formula (Ia)] can be made into a cephalosporin derivative of the formula (IX) by being acted on by ammonia in an organic solvent to cause a ring closure.

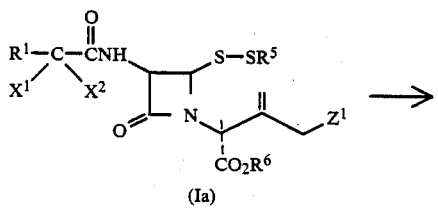

(Ia)

-continued

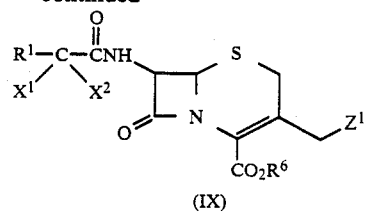

(IX)

In the formulae, $R^1$, $R^5$, $R^6$, $X^1$, $X^2$ and $Z^1$ are as defined above.

Examples of the organic solvents useful in the foregoing reaction include a wide variety of those inert among which it is preferred to use dimethylformamide, dimethylacetamide and like nonprotonic polar solvents, and more preferable to use is dimethylformamide. The amounts of the compound of the formula (I) and ammonia to be used are not particularly limited and can be adequately determined over a wide range. The ammonia is used in an amount of usually about 1 to about 10 moles, preferably about 1 to about 3 moles, per mole of the compound of the formula (I). The reaction favorably proceeds at a temperature of usually about −78° to about 20° C., preferably about −40° to about 5° C. and is completed in up to about 1 to about 60 minutes.

The present invention will be described below in more detail with reference to the following Examples and Comparison Example in which Ph represents a phenyl group.

EXAMPLE 1

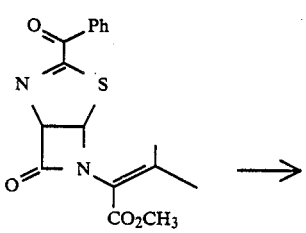

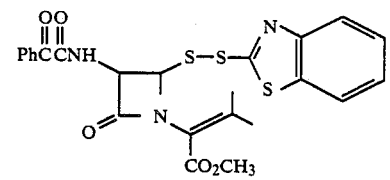

There were dispersed in 1 ml of tetrahydrofuran 11.2 mg of methyl 2-(3-benzoyl-7-oxo-4-thia-2,6-diazabicyclo[3,2,0]hepto-2-ene-6-yl)-3-methyl-2-butenate and 15.4 mg of dibenzothiazolyldisulfide. To the dispersion was added 0.25 ml of a 20% aqueous solution of perchloric acid and the mixture was stirred at room temperature for 24 hours. To the reaction mixture was added 5 ml of ethyl acetate and the insolubles were removed by a glass filter. The filtrate was washed with water and dried over anhydrous sodium sulfate and the solvent was distilled off. The residue (24.3 mg) was separated and purified by column chromatography on silica gel, giving 13.6 mg of methyl 2-(4-(2-benzothiazolyl)dithio-3-benzoylamido-2-oxoazetidine-1-yl)-3-methyl-2-butenate in a yield of 82%.

IR (CHCl$_3$): 3370, 1778, 1723, 1695, 1670 cm$^{-1}$.

NMR (CDCl₃): δ2.13 (s, 3H), 2.20 (s, 3H), 3.15 (s, 3H), 5.37 (dd, 1H, 4.7 Hz, 8 Hz), 5.62 (d, 1H, 4.7 Hz), 7.2–7.7 (m, 7H), 7.85 (d, 1H, 8 Hz), 8.2–9.0 (m, 2H).

EXAMPLES 2 TO 15

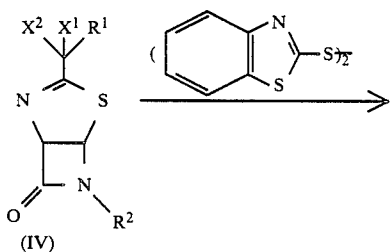

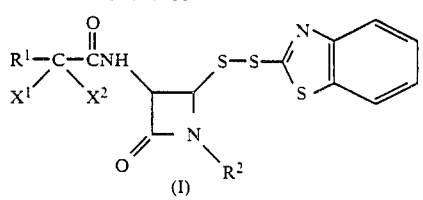

Thiazolinoazetidinone of the formula (IV) and dibenzothiazolyldisulfide were dispersed in tetrahydrofuran and an acid was added thereto. The mixture was stirred at room temperature over a period of time as shown in Table I below. The reaction was conducted under the same conditions as in Example 1 except those indicated in Table I below, and subsequently treated in the same manner as in Example 1 to provide a desired azetidinone derivative of the formula (I).

Table I below shows the reaction conditions and the yields, and Table II below indicates the data on IR and $^1$H NMR in respect of the derivatives (I).

TABLE I

| Ex. | Compound (IV) | | | | Acid | Reaction time hour | Yield (%) (I) | recovered (IV) |
|---|---|---|---|---|---|---|---|---|
| | $R^1$ | $X^1$ | $X^2$ | $R^2$ | | | | |
| 2 | Ph | =O | | ![structure with CO₂CH₃] | 5% HCl | 40 | 60 | 40 |
| 3 | Ph | =O | | ![structure with CO₂CH₃] | 5% HCl | 120 | 83 | — |
| 4 | Ph | =O | | ![tetrazole structure with CO₂CH₂Ph, CH₃] | 5% HCl | 14 | 65 | — |
| 5 | Ph | Cl | Cl | ![structure with Cl, CO₂CH₂Ph] | 20% HClO₄ | 24 | 53 | 32 |
| 6 | Ph | Cl | Cl | ![structure with Cl, CO₂CH₂Ph] | 12% HCl | 57 | 57 | — |
| 7 | Ph | Cl | Cl | ![tetrazole structure with CO₂CH₂Ph, CH₃] | 30% p-TsOH | 52 | 56 | 17 |
| 8 | Ph | Cl | Cl | ![tetrazole structure with CO₂CH₂Ph, CH₃] | 12% HCl | 47 | 63 | — |

TABLE I-continued

| Ex. | Compound (IV) R¹ | X¹ | X² | R² | Acid | Reaction time hour | Yield (%) (I) | recovered (IV) |
|---|---|---|---|---|---|---|---|---|
| 9 | Ph | Cl | Cl | (structure: CH₂=C(CH(CH₃)CO₂CH₂Ph)CH₂-S-tetrazole-N-CH₃) | 20% HClO₄ | 54 | 65 | 20 |
| 10 | Ph | Cl | Cl | (structure: CH₂=C(CH(CH₃)CO₂CH₂Ph)CH₂-S-tetrazole-N-CH₃) | 70% HClO₄ | 54 | 54 | 29 |
| 11 | Ph | =N—OCH₃ | | (structure: isopropenyl with CH(CH₃)CO₂CH₂Ph) | 20% HClO₄ | 72 | 38 | 38 |
| 12 | Ph | OCOCH₃ | H | (structure: isopropenyl with CH(CH₃)CO₂CH₂Ph) | 5% HCl | 2 | 75 | — |
| 13 | Ph | OH | H | (structure: isopropenyl with CH(CH₃)CO₂CH₂Ph) | 5% HCl | 0.6 | 56 | — |
| 14 | Ph | SC₆Cl₅ | H | (structure: CH₂=C(CH(CH₃)CO₂CH₂Ph)CH₂Cl) | 20% HClO₄ | 53 | 40 | — |
| 15 | PhO | SPh | H | (structure: CH₂=C(CH(CH₃)CO₂CH₂Ph)CH₂Cl) | 20% HClO₄ | 116 | 85 | — |

TABLE II

| Ex. | Compound (I) R¹ | X¹ | X² | R² | | |
|---|---|---|---|---|---|---|
| 4 | Ph | =O | | (tetrazolylthio-methylene structure with CO₂CH₂Ph) | IR (CHCl₃) | 3370, 1780, 1740, 1670 cm⁻¹ |
| | | | | | NMR (CDCl₃) δ | 3.78 (s, 3H), 4.23 (bs, 2H), 5.18 (s, 3H), 5.3–5.6 (m, 1H), 5.43 (s, 1H), 5.55 (s, 1H), 5.67 (d, 1H, 4Hz), 7.2–8.0 (m, 13H), 8.0–8.5 (m, 2H) |
| 5 | Ph | Cl | Cl | (CH₂=C(CH₂Cl) with CO₂CH₂Ph) | IR (CHCl₃) | 3380, 1782, 1740, 1700, 1500 cm⁻¹ |
| | | | | | NMR (CDCl₃) δ | 4.21 (s, 2H), 5.13 (s, 2H), 5.27 (s, 2H), 5.36 (dd, 1H, 4Hz, 8Hz), 5.55 (s, 1H), 5.57 (d, 1H, 4Hz), 7.28 (s, 5H), 7.2–7.6 (m, 5H), 7.6–8.0 (m, 5H) |
| 7 | Ph | Cl | Cl | (tetrazolylthiomethylene with CO₂CH₂Ph, N-CH₃) | IR (CHCl₃) | 3390, 1780, 1740, 1705, 1505 cm⁻¹ |
| | | | | | NMR (CDCl₃) δ | 3.74 (s, 3H), 4.18 (bs, 2H), 5.10 (s, 2H), 5.15 (s, 1H), 5.36 (s, 1H), 5.37 (dd, 1H, 5Hz, 8Hz), 5.50 (s, 1H), 5.64 (d, 1H, 5Hz), 7.1–7.5 (m, 10H), 7.5–8.0 (m, 5H) |
| 11 | Ph | =N—OCH₃ | | (isopropenyl with CO₂CH₂Ph) | IR (CHCl₃) | 3380, 1780, 1740, 1690, 1680 cm⁻¹ |
| | | | | | NMR (CDCl₃) δ | 1.93 (s, 3H), 4.02 (s, 3H), 5.00 (s, 1H), 5.08 (s, 1H), 5.19 (s, 3H), 5.63 (m, 2H), 7.30 (s, 5H), 7.3–7.9 (m, 10H) |

TABLE II-continued

| Ex. | R¹ | X¹ | X² | R² | | |
|-----|----|----|----|----|----|----|
| 12 | Ph | OCOCH₃ | H | (structure with CO₂CH₂Ph) | IR (CHCl₃)<br>NMR (CDCl₃) δ | 3390, 1778, 1745, 1738, 1696, 1510, 1423 cm⁻¹<br>1.92 (s, 3H), 2.17 (s, 3H), 4.93 (s, 1H), 5.00 (s, 1H), 5.13 (s, 3H), 5.48 (m, 2H), 6.20 (s, 1H), 7.1–7.9 (m, 15H) |
| 13 | Ph | OH | H | (structure with CO₂CH₂Ph) | IR (CHCl₃)<br>NMR (CDCl₃) δ | 3380, 1775, 1739, 1683, 1507 cm⁻¹<br>1.89 (s, 3H), 4.96 (bs, 2H), 5.13 (s, 2H), 5.13–5.20 (m, 2H), 5.29 (dd, 1H, 4Hz, 8.5Hz), 5.52 (d, 1H, 4Hz), 7.30 (s, 5H), 7.1–7.9 (m, 10H) |
| 14 | Ph | SC₆Cl₅ | H | (structure with Cl, CO₂CH₂Ph) | IR (CHCl₃)<br>NMR (CDCl₃) δ | 3380, 1780, 1735, 1673, 1330 cm⁻¹<br>4.24 (bs, 2H), 5.17 (s, 2H), 5.1–5.3 (m, 1H), 5.27 (bs, 2H), 5.33 (s, 1H), 5.41 (s, 1H), 5.55 (m, 1H), 7.2–8.0 (m, 15H) |
| 15 | Ph | SPh | H | (structure with Cl, CO₂CH₂Ph) | IR (CHCl₃)<br>NMR (CDCl₃) δ | 3400, 1783, 1740, 1690, 1490 cm⁻¹<br>4.32 (bs, 2H), 5.14 (s, 2H), 5.23 (s, 2H), 5.31 (s, 1H), 5.45–5.65 (m, 1H), 5.50 (bs, 1H), 5.83 (d, 1H, 5Hz), 7.2–8.0 (m, 20H) |

EXAMPLE 16

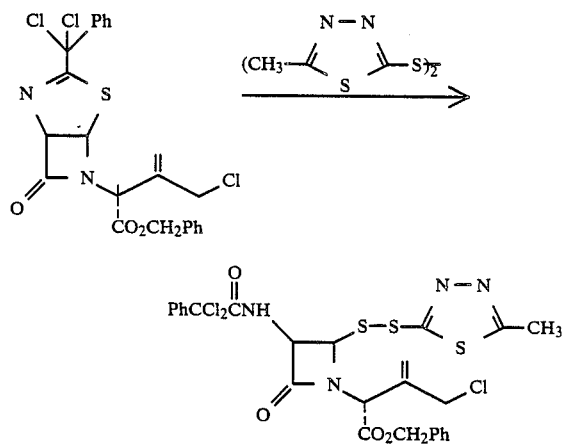

There were dispersed in 2 ml of tetrahydrofuran 111.9 mg of benzyl 2-(3-phenyldichloromethyl-7-oxo-4-thia-2,6-diazabicyclo[3,2,0]hepto-2-ene-6-yl)-3-chloromethyl-3-butenate and 79.6 g of di-5-methyl-1,3,4-thiadiazolyldisulfide. To the dispersion was added 0.5 ml of a 20% aqueous solution of perchloric acid and the mixture was stirred at room temperature for 70 hours. The subsequent treatment was carried out in the same manner as in Example 1, giving 107.3 mg of benzyl 2-(4-(5-methyl-1,3,4-thiadiazole-2-yl)dithio-3-phenyldichloroacetamide-2-oxazetidine-1-yl)-3-chloromethyl-3-butenate in 74% yield.

IR (CHCl₃): 3380, 1780, 1740, 1700, 1505 cm⁻¹.

NMR (CDCl₃): δ2.67 (s, 3H), 4.18 (s, 2H), 5.19 (s, 2H), 5.24 (s, 2H), 5.28 (dd, 1H, 5 Hz, 7 Hz), 5.48 (s, 1H), 5.64 (d, 1H, 5 Hz), 7.32 (s, 5H), 7.2–7.5 (m, 3H), 7.5–7.8 (m, 2H), 8.06 (d, 1H, 7 Hz).

EXAMPLE 17

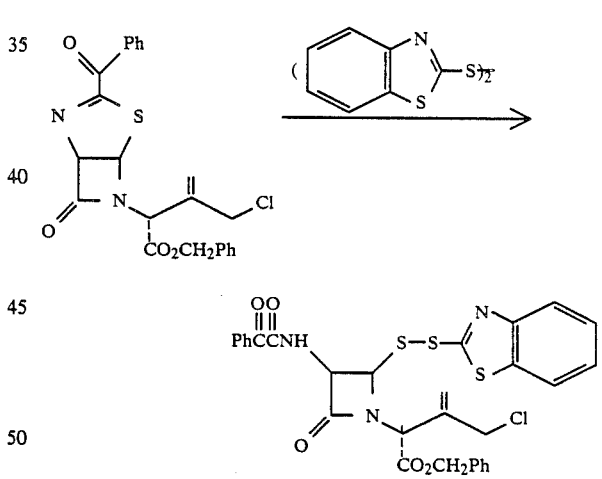

There were dispersed in 3 ml of acetone and 2 ml of methylene chloride 93.9 mg of benzyl 2-(3-benzoyl-7-oxo-4-thia-2,6-diazabicyclo[3,2,0]hepto-2-ene-6-yl)-3-chloromethyl-3-butenate and 77.3 mg of dibenzothiazolyldisulfide. To the dispersion was added 0.5 ml of a 10% aqueous solution of perchloric acid and the mixture was stirred at room temperature for 103 hours. The subsequent treatment was effected in the same manner as in Example 1, affording 99.0 mg of benzyl 2-(4-(2-benzothiazolyl)dithio-3-benzoylamide-2-oxoazetidine-1-yl)-3-chloromethyl-3-butenate in a yield of 75%.

IR (CHCl₃): 3370, 1780, 1740, 1670 cm⁻¹.

NMR (CDCl₃): δ4.26 (s, 2H), 5.20 (s, 2H), 5.28 (s, 1H), 5.32 (s, 1H), 5.3–5.56 (m, 1H), 5.56 (s, 1H), 5.66 (d, 1H, 4 Hz), 7.30 (s, 5H), 7.2–8.0 (m, 8H), 8.0–8.4 (m, 2H).

EXAMPLE 18

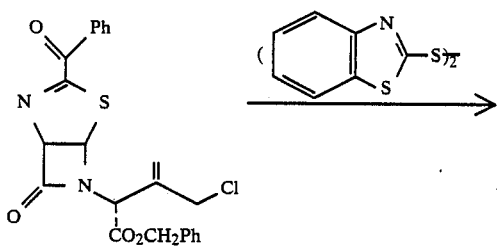

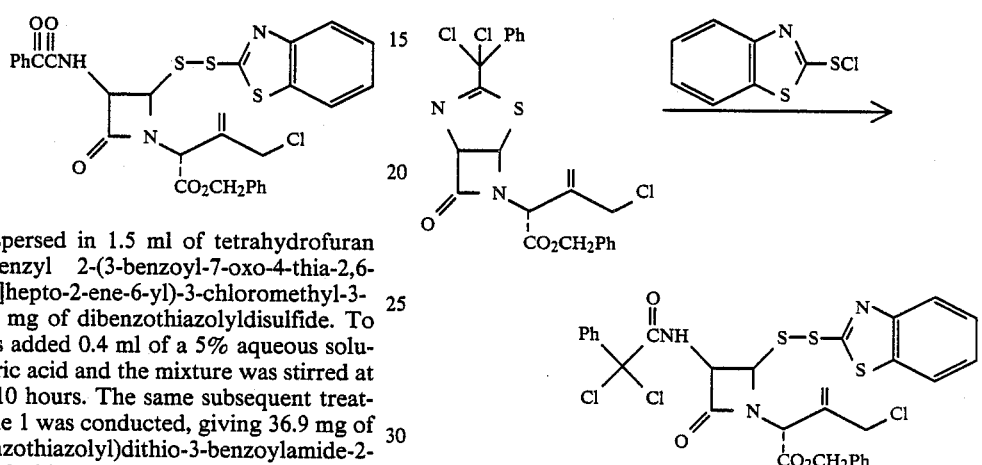

There were dispersed in 1.5 ml of tetrahydrofuran 39.1 mg of benzyl 2-(3-benzoyl-7-oxo-4-thia-2,6-diazabicyclo[3,2,0]hepto-2-ene-6-yl)-3-chloromethyl-3-butenate and 34.9 mg of dibenzothiazolyldisulfide. To the dispersion was added 0.4 ml of a 5% aqueous solution of hydrochloric acid and the mixture was stirred at 60° to 70° C. for 10 hours. The same subsequent treatment as in Example 1 was conducted, giving 36.9 mg of benzyl 2-(4-(2-benzothiazolyl)dithio-3-benzoylamide-2-oxoazetidine-1-yl)-3-chlorometyl-3-butenate in a 67% yield. The results of IR and NMR spectrum in respect of the product were found identical with those for the compound obtained in Example 17.

EXAMPLE 19

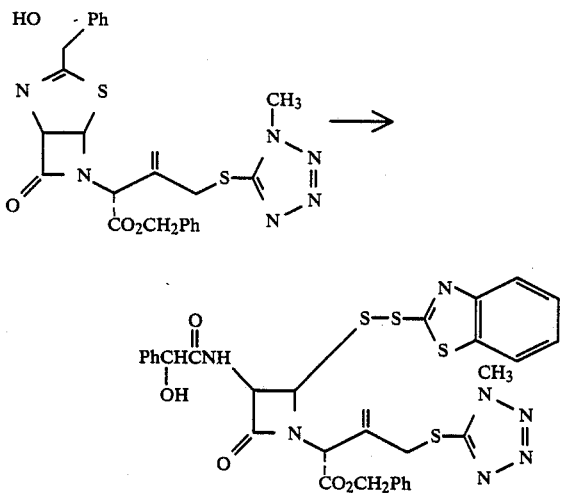

There were dispersed in 0.6 ml of tetrahydrofuran 14.3 mg of benzyl 2-(3-phenylhydroxymethyl-7-oxo-4-thia-2,6-diazabicyclo[3,2,0]hepto-2-ene-6-yl)-3-(1-methyl-1,2,3,4-tetrazole-5-ylthio)methyl-3-butenate and 10.6 mg of dibenzothiazolyldisulfide. To the disperion was added 0.15 ml of a 5% aqueous solution of hydrochloric acid and the mixture was stirred at room temperature for 1 hour. To the reaction mixture was added ethyl acetate and the insolubes were removed by a glass filter. The filtrate was washed with water and dried over anhydrous sodium sulfate. Then the solvent was distilled off, leaving 25 mg of the residue which was separated and purified by column chromatography on silica gel, affording 15.9 mg of benzyl 2-(4-(2-benzothiazolyl)dithio-3-phenylhydroxyacetamide-2-oxoazetidine-1-yl)-3-(1-methyl-1,2,3,4-tetrazole-5-ylthio)methyl-3-butenate in a yield of 83%.

IR (CHCl$_3$): 3380, 1778, 1742, 1685 cm$^{-1}$.

$^1$H NMR (CDCl$_3$): δ3.72 (s, 3H), 4.15 (bs, 2H), 4.0–4.5 (bm, 1H), 5.09 (s, 2H), 5.0–5.6 (m, 6H), 7.0–7.9 (m, 15H).

COMPARISON EXAMPLE

A 0.6 ml quantity of dioxane was added to 29.0 mg of benzyl 2-(3-phenyldichloromethyl-7-oxo-4-thia-2,6-diazabicyclo[3,2,0]hepto-2-ene-6-yl)-3-chloromethyl-3-butenate to obtain a uniform solution. To the solution was added 0.06 ml of a 5% aqueous solution of hydrochloric acid. The mixture was stirred at room temperature for 15 minutes.

Aside from the above procedure, 2 ml of dioxane was added to 37.9 mg of 2-benzothiazolyldisulfide and the mixture was heated in a hot water bath to obtain a uniform solution. To the solution was added 0.14 ml of a carbon tetrachloride solution containing 0.59M chlorine to undergo reaction for 15 minutes. The resulting reaction mixture was added to the foregoing dioxane solution and the mixture was stirred at room temperature for 30 minutes. The reaction mixture thus obtained was subjected to column chromatography on silica gel with use of ethyl acetate and the effluent was concentrated at reduced pressure. The residue was dissolved in benzene and the benzene was distilled off at reduced pressure, leaving colorless solids and a residual mixture as colorless oils which were subjected to chromatography on silica gel by using benzene and then benzene-ethyl acetate (10:1), recovering 29.0 mg of the starting material.

What is claimed is:

1. An azetidinone derivative represented by the formula (I)

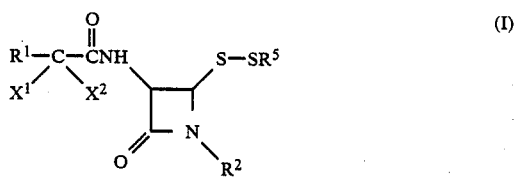

wherein:
R¹ is phenyl optionally substituted with methyl, chlorine or nitro, or phenoxy optionally substituted with methyl, chlorine or nitro;
R² is a group of the formula (II), (III), or (VI)

$$\underset{\underset{\text{COOR}^6}{|}}{\overset{\overset{\|}{\diagup}}{\diagdown}}\diagup\text{Z}^1 \qquad \text{(II)}$$

$$\underset{\text{COOR}^6}{\diagdown}\diagup\overset{\diagup\text{Z}^1}{\diagdown\text{Z}^2} \qquad \text{(III)}$$

$$\underset{\text{COOR}^6}{\diagdown}\diagup\overset{\diagup\text{Z}^1}{\diagdown\text{W}} \qquad \text{(VI)}$$

wherein R⁶ is hydrogen or carboxyl-protecting group; Z¹ and Z² are the same or different and are each hydrogen, halogen, methylthio, ethylthio, phenylthio, p-nitrophenylthio, pentachlorophenylthio, 2-pyridylthio, 2-benzothiadiazolylthio, 1,3,4-thiadiazole-5-ylthio, 1,2,3,4-tetrazole-5-ylthio, 1-methyl-1,2,3,4-tetrazole-5-ylthio, O-ethyldithiocaerbonate, N,N-diethyldithiocarbamate, phenylsulfonyl, p-methylphenylsulfonyl, hydroxy, methoxy, ethoxy, acetoxy, benzoyloxy, nitrosooxy, nitriloxy, dimethylamino, or piperidine-1-yl, and W is protected hydroxyl group;
X¹ and X² are the same or different and are halogen, hydroxyl, alkoxy, acyloxy, SR⁴ (wherein R⁴ is straight chain or branched chain lower alkyl, phenyl optionally substituted with chlorine or nitro, pyridyl, benzothiazolyl), amino or hydrogen, one of X¹ and X² not being hydrogen when the other is, or

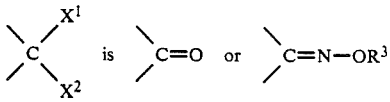

(wherein R³ is hydrogen, or lower alkyl); and
R⁵ is phenyl optionally substituted with chlorine or nitro, pyridyl, 2-benzothiazolyl, 1,3,4-thiadiazolyl optionally substituted with methyl or phenyl, tetrazolyl optionally substituted with methyl or phenyl, or benzimidazolyl.

* * * * *